United States Patent [19]

Tinti et al.

[11] Patent Number: 4,510,318

[45] Date of Patent: Apr. 9, 1985

[54] DITHIODIACYL CARNITINES

[75] Inventors: Maria O. Tinti; Emma Quaresima; Carlo Bagolini; Paolo de Witt, all of Rome, Italy

[73] Assignee: Sigma-Tau Industrie Farmaceutiche Riunite S.p.A., Rome, Italy

[21] Appl. No.: 570,190

[22] Filed: Jan. 12, 1984

Related U.S. Application Data

[62] Division of Ser. No. 359,732, Mar. 19, 1982.

[30] Foreign Application Priority Data

Mar. 31, 1981 [IT] Italy ............... 48167 A/81

[51] Int. Cl.³ ............... C07C 149/20; A61K 31/22
[52] U.S. Cl. ............... 560/147
[58] Field of Search ............... 560/147

[56] References Cited

U.S. PATENT DOCUMENTS 4,401,827 8/1983 de Witt ............... 560/147
4,443,475 4/1984 Cavazza ............... 560/147

FOREIGN PATENT DOCUMENTS 46-02247 1/1971 Japan ............... 560/253
2095676 10/1982 United Kingdom ............... 560/147

OTHER PUBLICATIONS

J. Biol. Chem., vol. 237, No. 12, Dec. 1962, pp. 3628-3632, Bremer, J., "Carnitine in Intermediary Metabolism".

Proc. Biol. Soc., vol. 89, 1963, pp. 26p-27p, Norum, K. R., "An Assay Method for the Palmitoyl-Coenzyme A-Carnitine Palmitoyltransferase".

Primary Examiner—Natalie Trousof
Assistant Examiner—Patricia M. Scott
Attorney, Agent, or Firm—Ladas & Parry

[57] ABSTRACT

Dithiodiacyl carnitines, intermediates for the preparation of mercaptoacyl-carnitines, are disclosed.

These mercapto acyl-carnitines are useful therapeutic agents, e.g. for the treatment of intoxications and burns and as mucolytic agents.

1 Claim, No Drawings

DITHIODIACYL CARNITINES

This is a divisional of co-pending application Ser. No. 359,732 filed Mar. 19, 1982.

The present invention relates to a novel class of carnitine derivatives and, more particularly, to mercapto acyl-carnitines wherein the mercapto acyl radical is the radical of saturated mercapto acids having from 2 to 10 carbon atoms.

The present invention also relates to the processes for the preparation of such mercapto acyl-carnitines and to pharmaceutical compositions containing same.

More specifically, the present invention relates to compounds having general formula:

$$(CH_3)_3 \overset{+}{N} - CH_2 - \underset{\underset{OR}{|}}{CH} - CH_2 - COOH \quad X^- \quad (I)$$

wherein:

$X^-$ is a pharmacologically acceptable halogenide ion, preferably the chloride ion, and R is the mercapto acyl radical of a saturated mercapto acid having from 2 to 10 carbon atoms.

This mercapto acyl radical is preferably selected from the group consisting of: mercapto acetyl, 2-mercapto propionyl, 3-mercapto propionyl, 2-mercapto butyryl, 3-mercapto butyryl, 4-mercapto butyryl and 5-mercapto valeryl. Correspondingly, the mercapto acyl carnitines preferred according to this invention are:

mercapto acetyl carnitine halogenide;
2-mercapto propionyl carnitine halogenide;
3-mercapto propionyl carnitine halogenide;
2-mercapto butyryl carnitine halogenide;
3-mercapto butyryl carnitine halogenide;
4-mercapto butyryl carnitine halogenide; and
5-mercapto valeryl carnitine halogenide.

The mercapto aryl-carnitines of formula (I) can be prepared e.g. by a process comprising the steps of:

(1) reacting carnitine hydrochloride with an halogen acyl chloride in the presence of an organic solvent inert towards the reaction at a temperature comprised between about 30 and about 60° C., thus obtaining the corresponding halogen acyl-carnitine; and (2) reacting at room temperature the halogen acyl-carnitine of step (1) with a compound selected from the class of alkali metal sulfides and acid sulfides, keeping the pH of the resulting reaction mixture substantially at neutrality by adding an inorganic acid selected between hydrochloric acid and sulfuric acid, thus obtaining the mercapto acyl-carnitine.

In step (1) the organic solvent is preferably trifluoro acetic acid.

In step (2) the compound selected from the class of the alkali metal sulfides and acid sulfides is preferably NaHS.

A preferred process for preparing the mercapto acyl-carnitines of general formula (I) comprises the following steps:

(a) reacting carnitine hydrochloride with an S-protected mercapto acyl halogenide selected among (1) the mercapto acyl halogenides wherein the SH group is protected with either trityl or p-substituted benzyl and (2) the dithio diacyl dihalogenides of formula

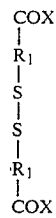

wherein:

X is a halogen atom, preferably chlorine and $R_1$ is an alkylene radical having from 1 to 9 carbon atoms, thus obtaining the corresponding S-protected mercapto acyl carnitine; and (b) removing by known per se techniques the protecting group of the S-protected mercapto acyl-carnitine of step (a).

In step (b), when the protective group is either trityl or p-methoxybenzyl, this protective group is removed by acid hydrolysis. When the protective group is p-nitrobenzyl, this group is removed by (1) converting the nitro group into amino group by hydrogenolysis, e.g. hydrogenating with a Parr hydrogenator at 30–50 psi in the presence of a palladium on carbon catalyst;

(2) treating the S-para amino benzyl derivative thus obtained with the Hopkins reagent and isolating the resulting mercapto acyl-carnitine mercury salt; and (3) treating the mercury salt thus obtained with $H_2S$ and isolating the resulting mercapto acyl-carnitine.

When in step (a) L-carnitine hydrochloride is reacted with the dithio diacyl dichloride, the product is a mixture of the corresponding dithio diacyl L-carnitine hydrochloride and dithio diacyl L-dicarnitine hydrochloride. After chromatographic resolution, either the former or the latter compound is converted into the corresponding mercapto acyl-carnitine by reacting it with Zn powder and hydrochloric acid.

Still a further process comprises reacting an acyl carnitine hydrochloride wherein the acyl radical is the radical of an unsaturated organic acid (e.g. crotonic acid) with $H_2S$ in the presence of a catalyst, e.g. azobisisobutyronitrile, thus obtaining the dithio diacyl dicarnitine hydrochloride which is then reduced with Zn powder and hydrochloric acid.

The following non-limiting examples illustrate the preparation and the chemico-physical characteristics of same compounds according to the present invention.

EXAMPLE 1

Preparation of 3-mercapto propionyl carnitine hydrochloride (V) (see the following reaction scheme)

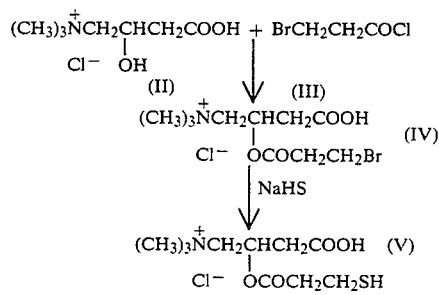

Preparation of 3-bromo propionyl carnitine hydrochloride (IV)

Carnitine hydrochloride(II) (0.01 moles) and 3-

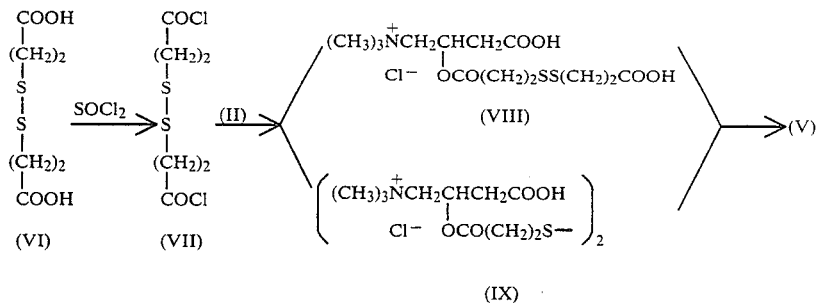

bromo propionyl chloride (III)(0.03 moles) were dissolved in an amount of trifluoro acetic acid sufficient to make the resulting reaction mixture homogeneous. The mixture was kept under magnetic stirring at a temperature comprised between 40° and 50° C. (reaction time: 18 hours). The reaction mixture was then cooled to room temperature and slowly poured in $Et_2O$ (200 ml). The residue which precipitated was washed with some small volumes of $Et_2O$, taken up with isopropanol and then precipitated with $AcOEt-Et_2O$. The raw residue was crystallized from acetone-methanol.

TLC ($CHCl_3$, MeOH, $NH_4OH$, $H_2O$, 55:35:5:5);
Anal. ($C_{10}H_{19}BrClNO_4$)C,H,Cl,N,
NMR ($D_2O$) $\delta = 2.87$ (2H, d, $-CH_2COOH$); 3.10–3.33 (11H, m, $-N^+-(CH_3)_3$ and $-\overline{OC}OCH_2-$); 3.50–3.93 (4H, m, $-CH_2-N^+ \leftarrow$ and $-CH_2Br$); 5.47–5.90

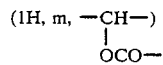

(1H, m, $-CH-$)
       |
      OCO—

Nucleophylic substitution of the bromine atom by the —SH group

A saturated solution of $NaHS.xH_2O$ in 15 cc of 95% ethanol was added very slowly to a solution of 3-bromo propionyl carnitine hydrochloride (3.3 grams; 0.01 moles) in 20 cc of absolute ethanol kept under magnetic stirring at room temperature and under a blanket of gaseous nitrogen. The pH was cheked constantly during the addition of the NaHS solution, having care that the pH were kept close to neutrality by HCl addition (even a slightly alkaline pH might cause degradation of bromo propionyl carnitine). The reaction mixture thus obtained was reacted overnight at room temperature. The mixture was then filtered. Upon ethyl ether addition to the filtrate, a precipitate was obtained which was crystallized from isopropanol. The product was kept constantly in an inert atmosphere. NMR analysis showed that this product was the title compound.

Anal. ($C_{10}H_{20}ClNO_4S$) C, H, Cl, N, S.
NMR ($D_2O$) $\delta = 2.80$–2.97 (6H, m, $-CH_2COOH$, and $-OCOCH_2CH_2SH$); 3.23 (9H, s, $N^+-(CH_3)_3$); 3.70–3.96 (2H, m, $-CH_2N^+ \leftarrow$); 5.47–5.93

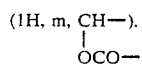

(1H, m, CH—).
       |
      OCO—

EXAMPLE 2

Preparation of 3-mercapto propionyl carnitine hydrochloride (V) (see the following reaction scheme)

Preparation of 3,3'dithio dipropionyl dichloride (VII)

3,3'dithio dipropionic acid (VI) (19 grams; 0.09 moles) was suspended in anhydrous toluene (300 ml.) and thionyl chloride (19 ml; 0.26 moles) was added to the resulting mixture which was then kept at 90° C. for 20 hours. 18 grams (yield: 77%) of 3,3'dithio dipropionyl dichloride (VII) were obtained which were used as such in the subsequent step.

Preparation of 3,3'dithio dipropionyl L-carnitine hydrochloride (VIII) and preparation of 3,3'dithio dipropionyl L-dicarnitine hydrochloride (IX)

L-carnitine hydrochloride (5 grams; 0.025 moles) was dissolved in trifluoro acetic acid (50 ml.). To the resulting solution the previously prepared dichloride (18 grams; 0.07 moles) was slowly added under stirring. The resulting reaction mixture was kept overnight under stirring at room temperature. The mixture was analyzed by TLC (eluant chloroform, methanol, isopropanol, acetic acid, water 40:40:15:15:10) and was shown to consist of two products having $R_f$ 0.3 and $R_f$ 0.6, respectively.

Ethyl ether was then added to the mixture and the precipitate which formed as treated with water. The excess of 3,3'dithio dipropionic acid was filtered off and the aqueous solution was lyophilyzed.

The lyophilyzed product was subjected to chromatography on a silica gel column buffered with 1.5% $Na_2HPO_4$. Eluant chloroform, methanol 50:50. The product having higher $R_f$ (3 grams; yield 30%) $[\alpha]_D = -27$ (C=1, $H_2O$) was thus isolated.

NMR analysis showed that the product was 3,3'dithio dipropionyl L-carnitine (VIII).

NMR $D_2O$ $\delta$

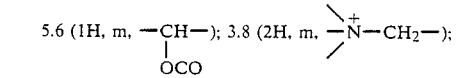

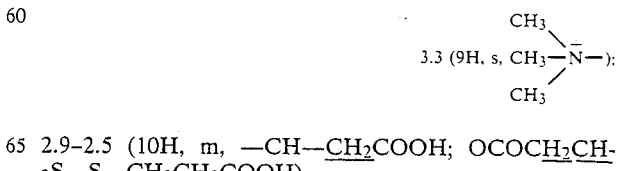

2.9–2.5 (10H, m, $-CH-\underline{CH_2}COOH$; $OCOC\underline{H_2}CH_2S-S-\underline{CH_2CH_2}COOH$).

By eluting with methanol, from the same silica-gel column the product having lower $R_f$ was isolated. 3.3 grams (yield 30%) were obtained. $[\alpha]_D = -28$. (C=1, $H_2O$).

NMR analysis showed that the product was 3,3'dithio dipropionyl L-dicarnitine (IX).

NMR $D_2O$ δ

5.8 (2H, m, 2—CH—); 3.8 (4H, m, 2-N⁺—CH₂;
                |
                OCO 3.2 (18H, s, 2 CH₃—N⁺—CH₃ / CH₃);

3.0–2.5 (12H, m, 2—CH—CH₂COOH)
                    |
                OCOCH₂CH₂S

Conversion of (IX) into (V)

3,3'dithio dipropionyl L-dicarnitine (IX) (1 gram; 0.003 moles) was dissolved in $H_2O$ (15 ml.) deareated with helium. To the resulting solution, concentrated HCl (1 ml.) and then, portionwise, zinc powder (250 mg.) were added. The resulting mixture was kept under stirring for 15 minutes and then filtered. In order to remove the $Zn\ Cl_2$ which formed, the aqueous filtrate was subjected to chromatography by a Chromatospak 100 Jobin Ivon preparative HPLC apparatus.

| Resin | Licroprep. RP18, 25–40 mμ, 100 grams |
|---|---|
| Pressure | 8 atmospheres |
| Eluant pressure | 6 atmospheres |
| Flow rate | 25 ml./minute |
| Eluant | $H_2O$-Acetonitrile (degassed with helium) 97:3 |
| Chromatographied product | 1 g/25 ml. $H_2O$ |

The eluted fractions were checked with a Waters model 401 HPLC apparatus.

| Resin | μ Bondapak C18 |
|---|---|
| Pressure | 1600 psi |
| Flow rate | 1 ml./minute |
| Detector | RI |
| Chart speed | 0.5 cm/minute. |

The fraction containing (V) ($R_f$ 6.4) was lyophilized away from light and stored under a blanket of Argon. 0.5 grams (yield: 90%) were obtained.

NMR $D_2O$ δ

5.8 (1H, m, —CH—); 3.8 (2H, m, —N⁺—CH₂—);
              |
              OCO 3.2 (9H, s, CH₃—N⁺—CH₃ / CH₃);

2.9–2.5 (6H, m, —CH—CH₂COOH; —OCOCH₂CH₂SH).

EXAMPLE 3

Preparation of 3-mercapto butyryl carnitine hydrochloride (X) (see the following reaction scheme)

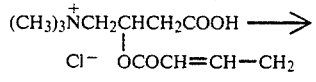

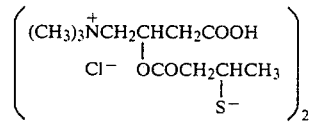

(XII)

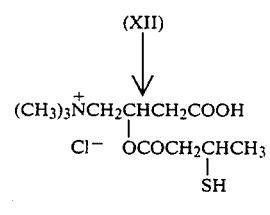

(X)

Preparation of 3,3'dithio dibutyryl dicarnitine hydrochloride (XII)

Crotonoyl carnitine hydrochloride (XI) (5 grams; 0.019 moles) was dissolved in ethanol and to the resulting solution catalytic amounts of azobis isobutyronitrile were added. The resulting solution was kept under stirring at 50° C. for 7–10 days and was periodically saturated with $H_2S$. Upon reaction termination, the ethanol-containing phase was concentrated and the oily residue thus obtained was repeatedly crystallized from ethanol-ethyl ether. About 5 grams (yield: 42%) of (XII) were obtained.

NMR $D_2O$ δ5.7

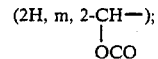

3.8–3.3 (6H, m, 2→N⁺—CH₂—; —CH—S—S—CH—);

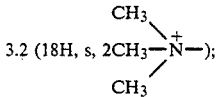

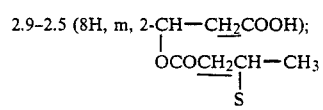

1.3 (6H, m, 2-S—CH—CH₃).

Conversion of (XII) into (X)

(XII) (5 grams; 0.008 moles) obtained in the previous step, was dissolved in 100 cc of degassed $H_2O$ and 5.5 cc of conc. HCl. To this solution 300 mg. of Zn were added and the resulting mixture was kept under stirring for 0.5 hour under an Argon blanket. The mixture was filtered, the filtrate was lyophilized and subjected to chromatography as illustrated in the previous Example. 1.5 grams (yield: 63%) of (X) were obtained.

NMR D$_2$O δ

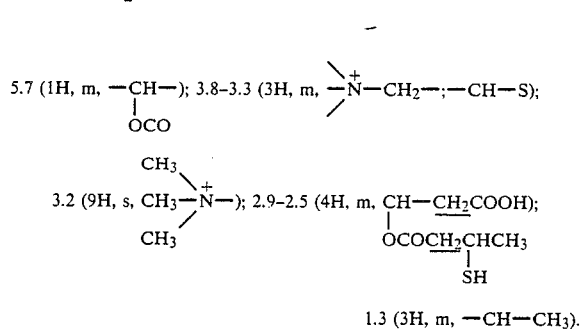

1.3 (3H, m, —CH—C$\underline{H}_3$).

EXAMPLE 4

Preparation of 4-mercapto butyryl carnitine hydrochloride (XIII) (see the following reaction scheme)

NMR D$_2$O δ

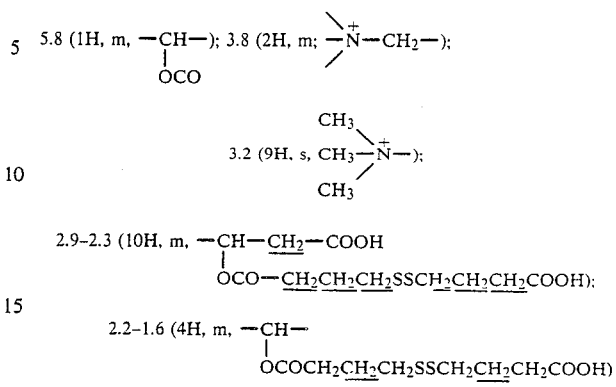

NMR analysis showed that this product was the compound (XVI).

Product at lower R$_f$

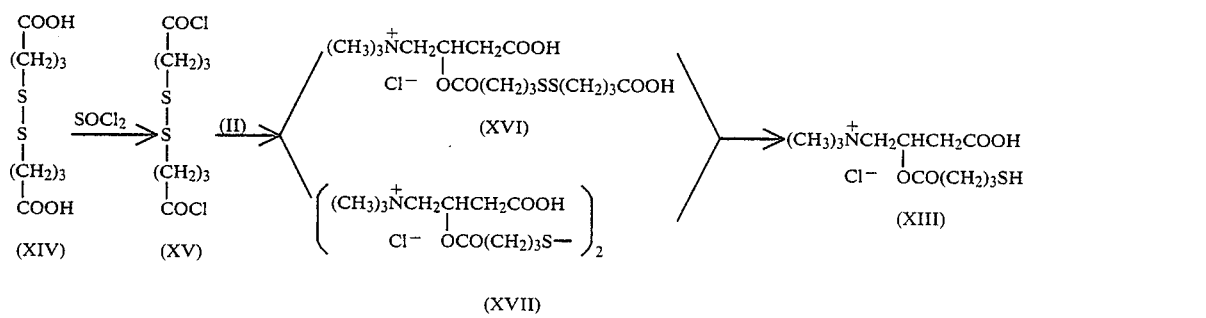

Preparation of 4,4'dithio dibutyryl dichloride (XV)

4,4'dithio dibutyric acid (XIV) (23.8 grams; 0.1 moles) was suspended in anhydrous toluene (200 cc.) and to the suspension thionyl chloride (35 grams; 0.3 moles) was added. The resulting mixture was kept at the reflux temperature for 4 hours, then concentrated under vacuum, washed with anhydrous toluene and dried. 25 grams (yield: 81%) of (XV) were obtained which were all used as such in the subsequent step.

Preparation of 4,4'dithio dibutyryl-carnitine hydrochloride (XVI) and of 4,4'dithio dibutyryl L-dicarnitine hydrochloride (XVII)

(II) (6 grams; 0.003 moles) was dissolved in trifluoro acetic acid (50 ml.). To the resulting solution (XV) (25 grams; 0.09 moles) was slowly added under stirring. The resulting mixture was kept under stirring overnight at room temperature.

The mixture was analyzed by TLC (chloroform, methanol, isopropanol, acetic acid, water 60:40:10:15:15) and was shown to consist of two products having R$_f$ 0.2 and R$_f$ 0.6 respectively.

To the reaction mixture ethyl ether was added, the precipitate which thus formed was washed with H$_2$O, the excess acid was removed and the aqueous solution was lyophilized. The lyophilyzed product was subjected to chromatography on a silica-gel column buffered with 1.5% Na$_2$HPO$_4$ (eluent chloroform, methanol 50:100). 2.2 grams of the product at higher R$_f$ and 3.5 grams of the product at lower R$_f$ were obtained. Product at higher R$_f$ [α]$_D$ = −26 (C=1, H$_2$O).

NMR D$_2$O δ

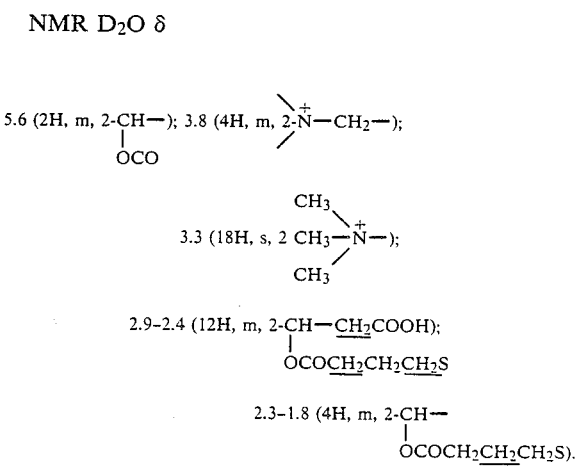

NMR analysis showed that this product was the compound (XVII).

Conversion of (XVII) into (XIII)

(XVII) (1 gram; 0.002 moles) was dissolved in 15 ml. of H$_2$O deareated with helium. To the resulting solution 1.5 ml. of conc. HCl and 700 mg. of Zn powder were added. Zinc addition was carried out slowly and portionwise. The resulting mixture was kept under stirring for about 30 minutes and then filtered. In order to remove ZnCl$_2$ which formed, the solution was subjected to chromatography at the same conditions as those outlined in Example 3.

The eluted solutions were also checked as indicated in Example 3.

The fraction containing the compound (XIII) (R$_f$ 6.46) was lyophilyzed away from light and stored under an Argon blanket.
NMR D$_2$O δ

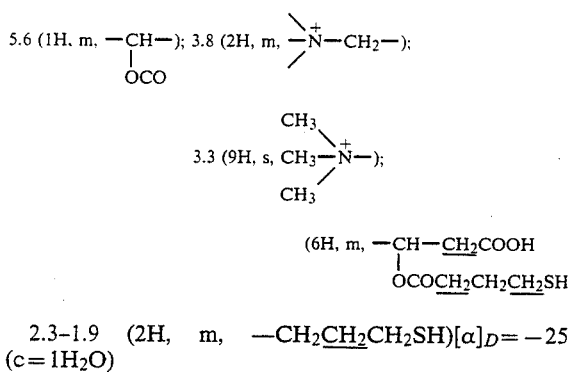

2.3–1.9  (2H, m, —CH$_2$CH$_2$CH$_2$SH)[α]$_D$= —25 (c=1H$_2$O)

It has been found that the mercapto acyl-carnitines of formula (I) are useful therapeutic agents for the treatment of intoxications, for the treatment of burns and the diseases of epithelia (and in general whenever it is important to restore to normal the metabolic cellular equilibrium unbalanced by exogenous and endogenous factors) and as mucolytic agents.

It is known that lack of sulphydryl groups SH available for the metabolism requirements, as well as the inability of the organism to utilize such groups in specific pathological situations, constitute the primary factor of anatomical and functional alterations of some body tissues. Indeed, the activity of most of the enzymes present in the cells of vital organs, such as liver, is related to the presence of SH groups in their molecules as well as to the activity of SH groups at the membrane level.

It is also known that the organism, when because of various reasons is unable to utilize the sulphydryl groups indispensable for the cellular metabolism to take place regularly, can utilize the sulphydryl groups that it derives from the administration of compounds containing such groups.

It has been difficult up to now to have available compounds able to cross the biologic membranes and free the SH groups in order to re-constitute the cellular membranes and restore the enzyme activity.

It has now been found that the compounds of the present invention possess a remarkable ability to cross the biologic membranes and particularly the mithocondrial membranes.

Moreover, the mercapto acyl-carnitines provide, in addition to the SH groups, the energy related to the acyl groups (typically, acetyl) which is needed for essential metabolic processes to take place.

The characteristics of pharmacological activity of the compounds of general formula (I) are hereinbelow illustrated.

Acute toxicity

The acute toxicity of the compounds of general formula (I) has been studied in the mouse with the Weil method (Weil C. S., Biometr. J. 8, 249, 1952).

The LD50 values of some compounds illustrated in Table I, indicate that the compounds are remarkably well tolerated.

TABLE I

LD50, mg Kg$^{-1}$, ep in mice of some mercapto acyl-carnitines of general formula (I). Weil's method (N = 5, K = 4) Cl = hydrochloride.

| Compounds | LD50 | and | fiducial limits |
|---|---|---|---|
| mercapto acetyl carnitine Cl | 308 | | 266–350 |
| 2-mercapto propionyl carnitine Cl | 294 | | 257–345 |
| 3-mercapto propionyl carnitine Cl | 312 | | 267–357 |
| 2-mercapto butyryl carnitine Cl | 294 | | 244–294 |
| 4-mercapto butyryl carnitine Cl | 303 | | 257–349 |
| 5-mercapto valeryl carnitine Cl | 281 | | 233–328 |

Protection against X-ray exposure

The effect of the compounds of formula (I) towards the damages provoked by X-ray exposure was studied.

The experiment animals, Albino Wister rats, treated with the compounds under examination (30–40 mg Kg$^{-1}$ 1 hour before irradiation and 15 mg Kg$^{-1}$ per day in the subsequent 20 days) were irradiated and checked over a time period to detect the onset of toxic effects and the time of survival with respect to the control group.

In table II, the percentages of survival at the 10th, 15th and 20th day from irradiation are reported.

TABLE II

Protective effect of some mercapto acyl-carnitines of general formula (I) towards the damage provoked by irradiation in rats. Percentage of surviving animals at various days from irradiation.

| Compounds | Days of survival | | |
|---|---|---|---|
| | 10 | 20 | 30 |
| Control | 80 | 20 | 10 |
| mercapto acetyl-carnitine Cl | 85 | 45 | 30 |
| 2-mercapto propionyl carnitine Cl | 80 | 70 | 45 |
| 3-mercapto propionyl carnitine Cl | 90 | 80 | 60 |
| 2-mercapto butyryl carnitine Cl | 100 | 85 | 70 |
| 4-mercapto butyryl carnitine Cl | 100 | 80 | 55 |
| 5-mercapto valeryl carnitine Cl | 95 | 70 | 50 |

Cutaneous regeneration

The ability of the compounds of formula (I) to speed up the cutaneous regeneration from burns has been tested in rabbits.

A 4 cm$^2$ cutaneous area of the average-top zone of the test animal back was burned.

The compounds were orally administered in aqueous solution at the dose of 20 mg Kg$^{-1}$ once a day for seven days. The area of cutaneous regeneration i.e. the area of the newly formed tissue was then measured (Table III).

TABLE III

Effect of compounds of formula (I) on cutaneous regeneration. Percentage of regenerated tissue at the 4th and 8th day from treatment.

| Compounds | Days | |
|---|---|---|
| | 4th day | 8th day |
| Control | 25 | 60 |
| mercapto acetyl-carnitine Cl | 35 | 70 |
| 2-mercapto propionyl carnitine Cl | 30 | 65 |
| 3-mercapto propionyl carnitine Cl | 40 | 80 |
| 2-mercapto butyryl carnitine Cl | 35 | 95 |
| 4-mercapto butyryl carnitine Cl | 25 | 70 |
| 5-mercapto valeryl carnitine Cl | 20 | 60 |

The expectorant and mucolytic activities of the compounds of formula (I) were determined.

Expectorant activity

The tests were carried out on male rabbits, weighing 2–3 Kg, anesthetized with ethyl urethane, by following the method disclosed by Perry et al. (J. Pharm. Exp. Ther. 73, 65, 1941).

The anesthetized animals, strapped head downward to an operating table at an inclination of 60°, had a cannula inserted in their trachea. Each cannula was connected to a feeding device which delivered a steady flow-rate of pre-heated air (36°–38° C.) at constant humidity (80%). At the lower end of each cannula, a graduated cylinder was fitted, wherein the bronchial secretion was collected. All of the animals breathed spontaneously and consequently they self-regulated the air intake suitable for normal respiration. After an hour following cannula insertion, the animals were administered orally (by stomach tube) the compounds of general formula (I) dissolved in distilled water at doses comprises between 20 and 40 mg. Each dose of drug was administered to 5 animals. The control animals (8) were given water only. The amount of secretion was determined after 1, 2 and 4 hours from administration. The results, summarized in Table IV, show that the compounds of general formula (I) do not exert expectorant activity.

Mucolytic activity

The tests were carried out in vitro by using the method disclosed by Morandini et al. (Lotta contro la tubercolosi 47, n. 4, 1977). A thromboelastograph was used to follow the variations induced by the compounds of general formula (I) and acetylcisteine on the rheological properties of human sputum. The results thereof, summarized in Table V, show that the test compounds bring about a greater decrease of human sputum density than that induced by acetylcysteine.

TABLE IV

| | Effects of compounds of general formula (I) on bronchial secretion | | | | |
|---|---|---|---|---|---|
| | | | Percentage variations ± s.e. of bronchial secretion versus values at the following intervals after administration | | |
| Number of animals | Treatment | | 1 hour | 2 hours | 4 hours |
| 8 | Controls | | +0.4 | +0.8 | +2.1 |
| 5 | mercapto acetyl carnitine | 10 mg oral | +0.3 | +0.9 | +2.4 |
| 5 | 2-mercapto propionyl carnitine Cl | 10 mg oral | +0.1 | +0.2 | +2.0 |
| 5 | 3-mercapto propionyl carnitine Cl | 15 mg oral | −0.2 | +0.4 | +1.1 |
| 5 | 2-mercapto butyryl carnitine Cl | 15 mg oral | +0.5 | +0.9 | +2.3 |
| 5 | 4-mercapto butyryl carnitine Cl | 20 mg oral | +0.4 | +0.6 | +1.2 |
| 5 | 5-mercapto valeryl carnitine Cl | 15 mg oral | +0.6 | −0.3 | +1.4 |

TABLE V

Mucolytic activity in vitro of compounds of general formula (I) and acetylcysteine; modifications of human sputum density

| | Percentage drop ± s.e. of the tracing versus maximum peak (*) after addition of 1 ml of a 10% solution of the test compounds at the diluitions indicated | |
|---|---|---|
| Compounds | 1/30 | 1/60 |
| mercapto acetyl carnitine Cl | 78.3 ± 5 | 45.2 ± 4 |
| 2-mercapto propionyl carnitine Cl | 85.4 ± 6 | 46.5 ± 6 |
| 3-mercapto propionyl carnitine Cl | 87.9 ± 7 | 48.2 ± 5 |
| 2-mercapto butyryl carnitine Cl | 85.3 ± 4 | 38.4 ± 5 |
| 4-mercapto butyryl carnitine Cl | 92.5 ± 7 | 45.8 ± 4 |

TABLE V-continued

Mucolytic activity in vitro of compounds of general formula (I) and acetylcysteine: modifications of human sputum density

| | Percentage drop ± s.e. of the tracing versus maximum peak (*) after addition of 1 ml of a 10% solution of the test compounds at the diluitions indicated | |
|---|---|---|
| Compounds | 1/30 | 1/60 |
| 5-mercapto valeryl carnitine Cl | 90.3 ± 6 | 48.3 ± 6 |
| Acetylcysteine | 75.7 ± 7 | 22.3 ± 4 |

(*) Mucolytic activity index

As experimentally shown, the compounds of this invention significantly modify the rheological properties of sputum. On perusal of the obtained results a decrease in sputum density at the larger doses (or lower dilutions) and at the smaller doses (or higher dilutions) constantly higher than that provoked by acetylcysteine, is detected. On the other hand no one of the compounds increases bronchial secretion nor is able to block the ciliary movement of the epithelium of trachea ring preparations in time intervals shorter than those permitted.

Effect on ciliary activity

The ability of the compounds of formula (I) to affect the ciliary motility was studied by observing with the microscope the ciliary movement of rat trachea rings soaked in solutions of the test compounds.

By this technique it is possible to study, with relation to compound concentration and contact time, the ciliary movement block provoked by the test compounds, which is related to mucus clearance from ciliary epithelium.

Substances to be used in the form of solutions must allow the foregoing block not to take place in less than fifteen minutes from contact.

2% aqueous solutions of the compounds of formula (I) provoked the ciliary movement block to take place in 18–20 minutes.

The compounds of the present invention are therapeutically useful for the treatment of burns and diseases of epithelia, for the treatment of the diseases of the respiratory tract and generally whenever it is important to restore to normal the metabolic cellular equilibrium of epithelia unbalanced by exogenous and endogenous factors. The patients in need thereof will be orally or parenterally administered a therapeutically effective amount of a mercapto acyl-carnitine of general formula (I).

The dose of mercapto acyl-carnitine of general formula (I) orally or parenterally administered will be generally comprised between about 2 and about 20 mg/Kg of body weight/day, although larger or smaller doses can be administered by the attending physician having regard to the age, weight and general conditions of the patient, utilizing sound professional judgement.

In practice, the mercapto acyl-carnitines are orally or parenterally administered in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials.

What is claimed is:

1. Dithio diacyl carnitines selected from the group consisting of 3,3'-dithiodipropionyl L-carnitine, 3,3'-dithiodipropionyl L-dicarnitine, 3,3'-dithiodibutyryl dicarnitine, 4,4'-dithiodibutyryl L-carnitine and 4,4'-dithiodibutyryl L-dicarnitine and the hydrochloride salts thereof.

* * * * *